United States Patent [19]
Nagatomo et al.

[11] 3,978,918
[45] Sept. 7, 1976

[54] HEATING AND COOLING DEVICE FOR AN AGITATOR TANK SERVING AS A FERMENTOR

[75] Inventors: Katuaki Nagatomo; Hiromasa Fukumori; Hiroyuki Narikiyo, all of Kudamatsu, Japan

[73] Assignee: Hitachi, Ltd., Japan

[22] Filed: Mar. 27, 1974

[21] Appl. No.: 455,404

[30] Foreign Application Priority Data
Mar. 28, 1973 Japan.......................... 48-36722[U]

[52] U.S. Cl............................... 165/109; 195/143; 259/DIG. 18; 165/163
[51] Int. Cl.².......................................... F28F 13/12
[58] Field of Search ........... 165/109, 163; 99/277.2; 159/25 A; 259/DIG. 18; 195/143

[56] References Cited
UNITED STATES PATENTS

| 964,941 | 7/1910 | Seymour | 165/163 |
|---|---|---|---|
| 2,070,951 | 2/1937 | Meldau | 165/172 X |
| 2,764,476 | 9/1956 | Etter | 165/109 X |
| 2,973,944 | 3/1961 | Etter | 165/109 X |

Primary Examiner—Albert W. Davis, Jr.
Attorney, Agent, or Firm—Craig & Antonelli

[57] ABSTRACT

A device for heating or cooling an agitator tank serving as a fermentor comprising a plurality of pipe blocks of the vertical trombone type each block consisting of a plurality of straight vertical pipes disposed in staggered relationship and connected to one another by U-shaped bent pipes and connected to the inner wall surface of the agitator tank, so that the pipe blocks are disposed radially in the tank.

15 Claims, 11 Drawing Figures

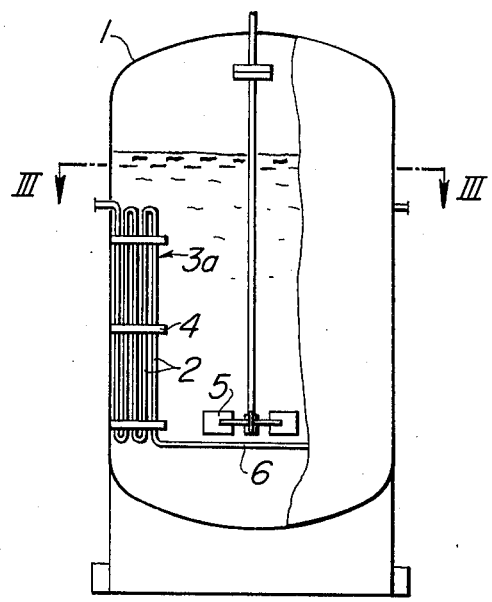
FIG. 1
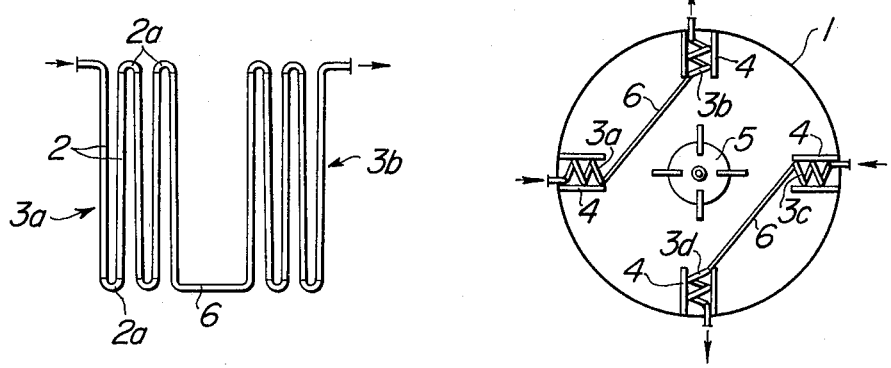
FIG. 2
FIG. 3

HEATING AND COOLING DEVICE FOR AN AGITATOR TANK SERVING AS A FERMENTOR

BACKGROUND OF THE INVENTION

This invention relates to heating and cooling devices, and more particularly it is concerned with a heating and cooling device for an agitator tank serving as a fermentor in which pipe blocks of the vertical trombone type are connected to the inner wall surface of the agitator tank so that they are disposed radially in the tank to effect heating and cooling of the content of the tank.

In heating or cooling the content of an agitator tank, it has hitherto been customary to be done by use of a heating and cooling device which is arranged on the outside of the agitator tank to act on the content thereof from outside, or a device which is arranged within the inside of the agitator tank to act on the content thereof from inside. Sometimes, these two devices have been employed simultaneously. In heating or cooling an agitator tank of a high capacity, for example, the use of a jacket shell alone which is mounted on the outside of the agitator tank is not enough to provide a sufficiently large heat transfer surface area to heat or cool the content of the tank satisfactorily. It is thus usual practice to use, in combination with the jacket shell, a ring-shaped coil which is mounted concentrically with the wall of the agitator tank.

The heating and cooling devices of the prior art mounted in an agitator tank have been unable to achieve satisfactory results in heating or cooling the content of the tank to permit such device to be employed for practical use because of the fact that the heat transfer surface is too small in area to have effect in transferring heat and for other reasons. The piping of such heating and cooling devices is so complex that difficulty is experienced in thoroughly cleaning the interior of the tank, thereby causing the accumulation of saprophytes in the tank.

In the case of a heating and cooling device in which a ring-shaped coil is disposed in the agitator tank or snaked pipes are arranged to form walls arranged in square form along the wall of the tank, the interior of the tank is separated by the heating and cooling device into different zones, so that satisfactory results cannot be achieved in agitating the liquid in the tank. In one type of heating and cooling device known in the art, the straight pipes of the vertical type disposed in the aagitator tank are joined by welding to the wall of the tank because dissimilar materials are used for the pipes and tank. The difference in the materials used results in the difference in thermal expansion between them, so that thermal stresses applied to the materials are increased and there are the possibilities of fractures in the welds of the pipes in service.

SUMMARY OF THE INVENTION

This invention has as its object the provision of a heating and cooling device for an agitator tank serving as a fermentor comprising at least two pipe blocks of the vertical trombone type which can concurrently serve as baffle members, so that the device can achieve satisfactory results not only in heating or cooling the content of the tank but also in agitating the content of the tank.

The invention has outstanding characteristics which are as follows:

1. The heating and cooling device comprises a plurality of pipe blocks of the vertical trombone type each block consisting of vertical straight pipes arranged in staggered relationship, so that the device can achieve increased results in transferring heat.

2. The increase in the degree of efficiency with which heat is transferred results in an increase in the heating or cooling capacity of the tank, thereby increasing productivity.

3. More than two pipe blocks of the vertical trombone type each consisting of vertical straight pipes arranged in staggered relationship and disposed in the vicinity of the inner wall surface of the agitator tank can concurrently serve as baffle members, thereby increasing the degree of efficiency with which agitation is effected.

4. The heating and cooling device comprising a plurality of pipe blocks of the vertical trombone type each consisting of vertical straight pipes arranged in staggered relationship has a greater heat transfer surface area than a device comprising a ring-shaped coil or vertical straight pipes or snaked pipes arranged in a conventional manner.

5. Since the device according to the invention has a greater heat transfer surface area than conventional devices, the use of a jacket shell mounted outside the tank can be eliminated. Thus, the agitator tank is only provided with a heating and cooling device mounted inside the tank so that the thickness of the wall of the agitator tank can be reduced because no pressure is applied to the tank from outside.

6. The use of vertical straight pipes connected to one another by U-shaped bent pipes eliminates the need to perform a pipe bending operation which must be performed in producing a ring-shaped coil for the device using it, thereby enabling to reduce cost. The device according to the invention has a smaller number of pipe inlets and outlets than the heating and cooling device comprising straight pipes or snaked pipes arranged in a conventional manner, thereby also enabling to reduce cost.

7. Since the heating and cooling device of the vertical trombone type is simple in construction and has no more projections than are necessary, so that washing and cleaning of the agitation tank can be effected readily by flushing through a nozzle mounted in the upper portion of the tank.

8. The U-shaped bent pipes used for interconnecting the vertical straight tubes to form a pipe block is resilient, so that the difference in thermal expansion between the agitation tank and the straight pipes arising from the use of dissimilar materials for them can be absorbed by the bent pipes.

BRIEF DESCRIPTION OF THE DRAWINGS

FIG. 1 to FIG. 3 shows one embodiment of this invention, FIG. 1 showing, in cross-section, a portion of an agitator tank provided with the heating and cooling device of the upright trombone type comprising upright straight pipes arranged in staggered relationship, FIG. 2 being a developmental view of a pipe block of the vertical trombone type, and FIG. 3 being a sectional view taken along the line III—III of FIG. 1;

DETAILED DESCRIPTION OF A PREFERRED EMBODIMENT

To enable the features of the present invention to be readily understood, heating and cooling devices of the prior art will be briefly outlined first of all with reference to FIG. 4 to FIG. 11.

Figure 4:
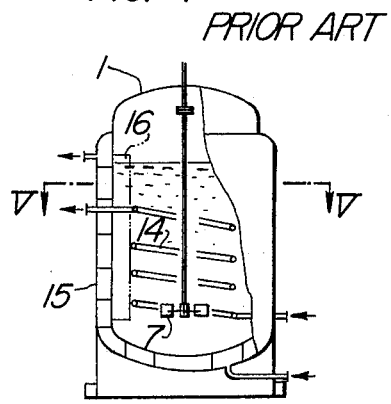
FIG. 4 is a front view of a heating and cooling device of the prior art.
Figure 5:
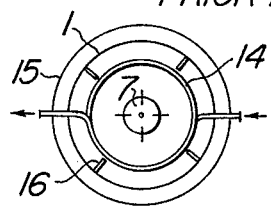
FIG. 5 is a sectional view taken along the line V—V of FIG. 4.

In FIG. 4 and FIG. 5, there is shown a heating and cooling device comprising a ring-shaped coil 14 forming convolutions concentric with the wall of an agitator tank 1 which is low in the degree of efficiency with which heat is transferred. The heating and cooling device also comprises a baffle member 16 interposed between the wall of the agitator tank 1 and the ring-shaped coil. The baffle member 16 is unable to achieve satisfactory results in agitating the content of the tank because the ring-shaped coil 14 form a sort of an inner tank in the interior of the agitator tank 1. The agitator tank 1 used as a fermentor operates on a batch system in which the tank is driven for rotation for a predetermined time and its rotation is interrupted for another predetermined time. The interior of the agitator tank should be washed and cleaned each time its operation is interrupted and the liquid contained therein is withdrawn before the next following operation is started. The presence of the ring-shaped coil of the heating and cooling device in the agitator tank makes it difficult to clean the tank thoroughly, and the provision of baffle member 16 adds to the difficulty experienced in effecting cleaning, thereby prolonging the time required for performing cleaning. Moreover, a large volume of steam or other agent is required for carrying out sterilization.

Figure 6:
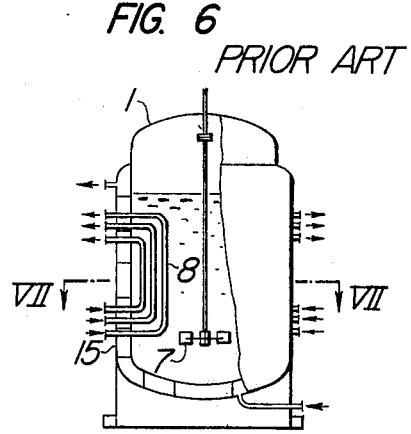
FIG. 6 is a front view of another heating and cooling device of the prior art.
Figure 7:
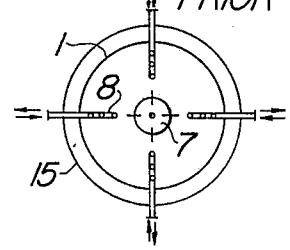
FIG. 7 is a sectional view taken along the line VII—VII of FIG. 6.

The heating and cooling device shown in FIG. 6 and FIG. 7 comprises a plurality of groups of vertical straight pipes 8 each group consisting of a number of vertical straight pipes disposed adjacent one another and arranged in a row extending from the wall of the agitation tank 1 toward the center thereof, so that the groups of vertical pipes 8 are arranged radially in the tank 1. The vertical straight pipes 8 of each group are bent outwardly at upper and lower ends, so that inlets and outlets of a heating or cooling medium are disposed outside the tank 1. This heating and cooling device has a small heat transfer surface area because limitations are placed on the distance between the outlets and inlets of the vertical straight pipes 8 and the distance between the outer edge of each agitator vane 7 and the vertical straight pipes 8. Moreover, since the heating and cooling device of this type has a large number of inlets and outlets of the straight pipes, production cost is increased because the expenses for joining the outlets and inlets to the tank 1 by welding are high. In addition, the provision of a large number of inlets and outlets results in an increase in the number of localities at which saprophytes are accumulated, thereby making it difficult to clean the tank thoroughly.

Since the outlets and inlets of the vertical straight pipes 8 are joined by welding to the agitator tank 1, there is a difference in thermal expansion between the straight pipes and the agitator tank when they are made of dissimilar materials, and the difference produces thermal stresses which are very high at the inlets and outlets of the straight pipes, so that there are possibilities of fractures occurring in the welds of the pipes in service.

Figure 8:
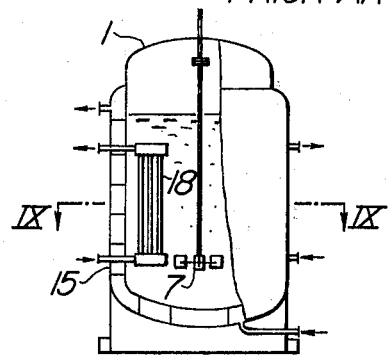
FIG. 8 is a front view of another heating and cooling device of the prior art.
Figure 9:
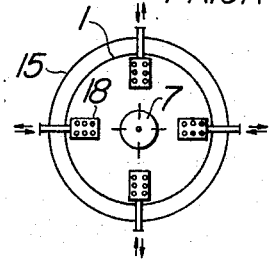
FIG. 9 is a sectional view taken along the line IX—IX of FIG. 8.

FIG. 8 and FIG. 9 show a heating and cooling device comprising a plurality of pipe blocks arranged radially in the tank 1 each comprising a number of minor diameter vertical straight pipes 18 disposed adjacent one another and arranged in rows extending from the wall of the agitator toward the center thereof, the pipes of each block being connected at their inlets to a major diameter pipe disposed at right angles to the straight pipes 18 and at their outlets to another major diameter pipe disposed at right angles to the pipes 18, the two major diameter pipes extending through the wall of the agitator tank outwardly thereof.

In the heating and cooling device of this type, a heating medium or cooling medium is introduced into each horizontal major diameter pipe of each pipe block and then moved into a large number of vertical minor diameter pipes. Thus, the rate of flow of the stream of heating or cooling medium through one vertical minor diameter pipe differ from the rates of movement of the medium through other vertical minor diameter pipes, so that the device cannot achieve satisfactory results in transferring heat.

The provision of the horizontal major diameter pipe on the upper ends of the vertical minor diameter pipes 18 of each pipe block of this type of heating and cooling device makes it difficult to perform washing and cleaning of the agitator tank 1, thereby causing the accumulation of saprophytes in the tank 1.

Like the heating and cooling device shown in FIG. 6 and FIG. 7, the heating and cooling device shown in FIG. 8 and FIG. 9 the thermal stresses applied to the inlets and outlets of the pipe blocks by the difference in thermal expansion between the agitator tank 1 and the pipes are very high when the tank and the pipes are made of dissimilar materials. Thus, there are possibilities of fractures of the welds of the pipes joined by welding to the agitator tank.

Figure 10:
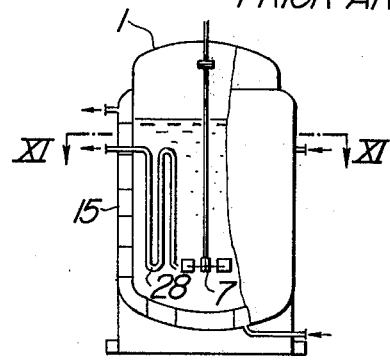
FIG. 10 is a front view of another heating and cooling device of the prior art.
Figure 11:
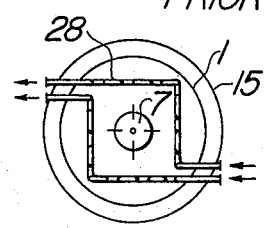
FIG. 11 is a sectional view taken along the line XI—XI of FIG. 10.

In the heating and cooling device shown in FIG. 10 and FIG. 11, snaked pipes are arranged to form walls disposed in square form along the wall of the agitator tank 1. Like the heating and cooling device shown in FIGS. 4 and 5, the heating and cooling device shown in FIG. 10 and FIG. 11 has a sort of a tank formed in the agitator tank 1, with the result that a portion of the content of the agitator tank 1 interposed between the inner wall surface of the agitator tank 1 and the outer surfaces of the straight pipes is not agitated thoroughly. Thus, the device is unable to achieve satisfactory results in agitating the whole content of the tank 1.

An embodiment of the invention will now be described with reference to FIG. 1 to FIG. 3. FIG. 1 is a front view of a portion of an agitator tank, shown in section, which is provided with the heating and cooling device comprising a plurality of pipe blocks of the vertical trombone type each consisting of vertical straight pipes arranged in staggered relationship, FIG. 2 is a developmental view of the pipe blocks of the vertical trombone type, and FIG. 3 is a sectional view taken along the line III—III of FIG. 1.

In the drawings, pipe blocks 3a, 3b, 3c and 3d are connected at one end thereof to the inner wall surface of the agitator tank 1 and are disposed radially in the tank 1. Each pipe block consists of a plurality of vertical straight pipes 2 arranged in staggered relationship and connected to one another at upper and lower ends thereof by U-shaped bent pipes 2a. 4 designates support plates supporting the vertical straight pipes 2 and connecting the same to the inner wall surface of the tank 1. 5 designates agitator vanes. As shown in FIG. 3, the pipe blocks 3a and 3b and 3c and 3d are connected to each other by a connector pipe 6. By moving a heating medium or cooling medium through the pipe blocks as indicated by arrows in FIG. 2 and FIG. 3, the content of the agitator tank 1 can be heated or cooled.

As shown in FIG. 3, there are provided four pipe blocks 3a, 3b, 3c and 3d in the present embodiment. It is to be understood that the invention is not limited to this specific number of the pipe blocks and that the number of pipe blocks may be increased or decreased according to the area of the heat transfer surface required for effecting heating or cooling satisfactorily.

In operation, actuation of the agitator vanes 5 agitates the liquid in the agitator tank 1 so that the liquid may move about in a stream in the tank and successively come into contact with the pipe blocks 3a, 3b, 3c and 3d. Since the pipe blocks 3a, 3b, 3c and 3d are connected to the wall of the tank 1, the rate of flow of the stream is sufficiently high to form a vortex in front of each pipe block. The vortex formed in front of each pipe block causes turbulence in the stream of liquid moving about in the tank 1, so that satisfactory results can be achieved in agitating the liquid. Thus, each pipe block concurrently serves as a baffle member, in addition to functioning as heating or cooling means.

The arrangement in which the vertical straight pipes 2 of each pipe block 3a, 3b, 3c or 3d are arranged in staggered relationship results in various portions of the liquid in the tank 1 impinging on the pipes 2 at the same speed. The arrangement in which the straight pipes are connected to one another by U-shaped bend pipes has the effect of causing the heating medium or cooling medium to flow at the same rate through the pipes 2 of each pipe block 3a, 3b, 3c or 3d. Thus, the whole liquid in the agitator tank 1 can be heated or cooled uniformly, thereby achieving satisfactory results in heating or cooling the liquid in the tank 1.

We claim:

1. A heat exchange device for a tank having an agitator and serving as a fermentor, said device comprising a plurality of pipe blocks of the vertical trombone type, each block consisting of a plurality of vertical straight heat exchange fluid pipes disposed in staggered relationship about a line extending radially within the tank, said agitator means creating flow substantially normal to the radially extending line so that fluid is in equivalent contact with the fluid pipes, and said fluid pipes being connected to one another by U-shaped bent pipes and connected to an inner wall surface of the tank, said pipe blocks being disposed radially in the tank.

2. A heat exchange device in a tank provided with agitator means, said device comprising:
   at least one block of plural generally vertical heat exchange fluid conduit means disposed radially within said tank, said conduit means being disposed in a staggered manner about a line extending radially within the tank said agitator means creating flow substantially normal to the radially extending line so that said fluid is in equivalent contact with the conduit means.

3. A heat exchange device according to claim 2, wherein said conduit means are interconnected such that heat exchange fluid can flow serially through the conduit means of said block.

4. A heat exchange device according to claim 3, wherein a plurality of spaced blocks are disposed about an inside wall of said tank, and wherein at least one pair of said blocks are serially connected in a fluid flow manner such that heat exchange fluid can flow serially from a first block to a second block of said at least one pair of blocks.

5. A heat exchange device according to claim 3, wherein said agitator means comprises agitator vane means disposed on agitator shaft means.

6. A heat exchange device according to claim 3, wherein said conduit means are interconnected such that heat exchange fluid can flow serially therethrough.

7. A heat exchange device according to claim 2, wherein said at least one block has an end connected to an inside wall of said tank.

8. A heat exchange device according to claim 7, wherein said tank has an inside circumference about which a plurality of said blocks are disposed.

9. A heat exchange device according to claim 2, wherein a plurality of spaced blocks are disposed about an inside wall of said tank, and wherein at least one pair of said blocks are serially connected in a fluid flow manner such that heat exchange fluid can flow serially from a first block to a second block of said at least one pair of blocks.

10. A heat exchange device according to claim 9, wherein connector conduit means interconnect a bottom portion of said first block with a bottom portion of said second block.

11. A heat exchange device according to claim 2, wherein a plurality of spaced blocks are disposed about an inside wall of said tank, and wherein at least one pair of said blocks are serially connected in a fluid flow manner such that heat exchange fluid can flow serially from a first block to a second block of said at least one pair of blocks.

12. A heat exchange device according to claim 2, wherein said agitator means comprises agitator vane means disposed on agitator shaft means.

13. A heat exchange device according to claim 2, wherein said agitator means comprises agitator vane means disposed on agitator shaft means.

14. A heat exchange device according to claim 2, wherein said conduit means are interconnected such that heat exchange fluid can flow serially therethrough.

15. A heat exchange device in a tank provided with agitator means, said device comprising:
   at least one block of plural generally vertical heat exchange fluid conduit means disposed within said tank,
   wherein said block extends within said tank in a given direction, and
   wherein said conduit means are successively disposed in a staggered manner about a line extending in a radial direction within the tank and the agitator means creates flow substantially normal to the radially extending line so that fluid is in equivalent contact with the conduit means.

* * * * *